United States Patent [19]
Skillicorn et al.

[11] Patent Number: 5,550,378
[45] Date of Patent: Aug. 27, 1996

[54] X-RAY DETECTOR

[75] Inventors: Brian Skillicorn, Saratoga; Giovanni Pastrone, Los Gatos, both of Calif.

[73] Assignee: Cardiac Mariners, Incorporated, Los Gatos, Calif.

[21] Appl. No.: 387,292

[22] Filed: Feb. 10, 1995

Related U.S. Application Data

[63] Continuation-in-part of Ser. No. 375,501, Jan. 17, 1995, abandoned, which is a continuation of Ser. No. 42,742, Apr. 5, 1993, abandoned, continuation-in-part of PCT/US94/03737, Apr. 5, 1994.

[51] Int. Cl.$^6$ ............................................. G01T 1/20
[52] U.S. Cl. ............................... 250/367; 250/368
[58] Field of Search ............................... 250/367, 368, 250/366

[56] References Cited

U.S. PATENT DOCUMENTS

| | | |
|---|---|---|
| 2,730,566 | 1/1956 | Bartow et al. |
| 3,114,832 | 12/1963 | Alvarez. |
| 3,593,243 | 7/1971 | Trump et al. |
| 3,605,750 | 9/1971 | Sheridan et al. |
| 3,611,032 | 10/1971 | Skillicorn. |
| 3,617,740 | 11/1971 | Skillicorn. |
| 3,684,991 | 8/1972 | Trump et al. |
| 3,890,521 | 6/1975 | Shroff. |

(List continued on next page.)

FOREIGN PATENT DOCUMENTS

| | | | |
|---|---|---|---|
| 58-92980 | 6/1983 | Japan | 250/368 |
| 58-210582 | 12/1983 | Japan | 250/368 |
| 64-39576 | 2/1989 | Japan | 250/368 |

OTHER PUBLICATIONS

Swinth et al., "Biomedical Probe Using a Fiber-optic Coupled Scintillator", *Medical Physics*, vol. 3, 1976, pp. 109–112.

W. C. Nixon, "High–resolution X–ray Projection Microscopy", vol. 232, *Proceedings of the Royal Society of London*, Nov., 1955, pp. 475–484.

George L. Clark, *The Encyclopedia of X–rays and Gamma Rays*, 1963, pp. 608–610, 617.

V. E. Cosslett et al., *X–ray Microscopy*, 1960, pp. 216–219, 296–303, 350–355, 368–369.

B. Skillicorn, "Insulators and X–Ray Tube Longevity: Some Theory and a Few Practical Hints", *Kevex Analyst*, 1983, pp. 2–6.

Howard H. Pattee, Jr., "The Scanning X–ray Microscope", *Journal Opt. Soc. Amer.*, vol. 43, 1953, pp. 61–62.

Lewis Etter, *The Science of Ionizing Radiation*, 1965, pp. 546–548.

R. M. Dolby et al., "A Spectrometer System for Long Wavelength X–ray Emission Microanalysis", *X–ray Microscopy and X–ray Microanalysis 1960*, pp. 351–357.

Russell H. Morgan et al., "Clinical Potentialities of Screen Intensifying Systems", Nov., 1949, vol. 62, No. 5, pp. 635–644.

Robert J. Moon, "Amplifying and Intensifying the Fluoroscopic Image by Means of a Scanning X–Ray Tube", vol. 112, *Science*, Oct. 6, 1950, pp. 389–395.

Howard H. Pattee, Jr., "Possibilities of the Scanning X–Ray Microscope", 1957, *X–Ray Microscopy and Microradiography*, pp. 367–375.

(List continued on next page.)

*Primary Examiner*—Carolyn E. Fields
*Assistant Examiner*—Edward J. Glick
*Attorney, Agent, or Firm*—Lyon & Lyon

[57] ABSTRACT

A detector having a plurality of densely packed x-ray detectors arranged into an array. Each detector preferably includes a scintillator element which is optically coupled to a photodetector element, preferably with a fiber optic link. Each photodetector element is preferably optically separate from adjacent photodetector elements. The detector array preferably includes integral an alignment structure to align the scintillator elements with the photodetector elements. The scintillator array elements are preferably formed from materials which possess a fast response and a minimum afterglow time.

4 Claims, 12 Drawing Sheets

U.S. PATENT DOCUMENTS

| | | |
|---|---|---|
| 3,925,660 | 12/1975 | Albert . |
| 3,949,229 | 4/1976 | Albert . |
| 3,983,397 | 9/1976 | Albert . |
| 3,992,631 | 11/1976 | Harte . |
| 4,007,375 | 2/1977 | Albert . |
| 4,032,787 | 6/1977 | Albert . |
| 4,048,496 | 9/1977 | Albert . |
| 4,057,745 | 11/1977 | Albert . |
| 4,104,526 | 8/1978 | Albert . |
| 4,144,457 | 3/1979 | Albert . |
| 4,149,076 | 4/1979 | Albert . |
| 4,196,351 | 4/1980 | Albert . |
| 4,206,361 | 6/1980 | Hounsfield et al. ........ 250/366 X |
| 4,234,794 | 11/1980 | Voinea et al. . |
| 4,259,582 | 3/1981 | Albert . |
| 4,259,583 | 3/1981 | Albert . |
| 4,260,885 | 4/1981 | Albert . |
| 4,284,891 | 8/1981 | Pergrale et al. ........ 250/368 X |
| 4,288,697 | 9/1981 | Albert . |
| 4,321,473 | 3/1982 | Albert . |
| 4,323,779 | 4/1982 | Albert . |
| 4,383,327 | 5/1983 | Kruger . |
| 4,465,540 | 8/1984 | Albert . |
| 4,519,092 | 5/1985 | Albert . |
| 4,532,425 | 7/1985 | Abileah et al. ........ 250/368 X |
| 4,573,183 | 2/1986 | Relihan . |
| 4,577,637 | 3/1986 | Mueller, Jr. . |
| 4,646,338 | 2/1987 | Skillicorn . |
| 4,694,480 | 9/1987 | Skillicorn . |
| 4,730,350 | 3/1988 | Albert . |
| 4,796,637 | 1/1989 | Mascuch et al. . |
| 4,873,708 | 10/1989 | Cusano et al. . |
| 4,945,894 | 8/1990 | Kawashima . |
| 4,967,121 | 10/1990 | Nero . |
| 4,974,929 | 12/1990 | Curry . |
| 4,990,785 | 2/1991 | Logan ........ 250/368 |
| 5,029,338 | 7/1991 | Aichinger et al. . |
| 5,132,539 | 7/1992 | Kwasnick et al. . |
| 5,140,162 | 8/1992 | Stettner . |
| 5,153,438 | 10/1992 | Kingsley et al. . |
| 5,171,232 | 12/1992 | Castillo et al. . |
| 5,185,773 | 2/1993 | Blossfeld et al. . |
| 5,187,369 | 2/1993 | Kingsley et al. . |
| 5,198,673 | 3/1993 | Rougeot et al. . |
| 5,203,777 | 4/1993 | Lee . |
| 5,231,654 | 7/1993 | Kwasnick et al. . |
| 5,231,655 | 7/1993 | Wei et al. . |
| 5,237,598 | 8/1993 | Albert . |
| 5,267,296 | 11/1993 | Albert . |
| 5,276,604 | 1/1994 | Messman . |
| 5,293,417 | 3/1994 | Wei et al. . |
| 5,303,282 | 4/1994 | Kwasnick et al. . |
| 5,304,898 | 4/1994 | Kataoka et al. . |

OTHER PUBLICATIONS

Center for Devices and Radiological Health, *Radiological Health Bulletin,* "FDA Draws Attention to Concerns about Radiation Risk from Fluoroscopy", Aug., 1992, pp. 1–3, 5.

Philips Photonics, "xP1700 Multichannel Photomultipliers", *XP1700 family of Multi–channel Photomultipliers—Philips Photonic Handbook,* at least by Dec., 1993, pp. 1–15.

Digiray, "Digiray's Reverse Geometry X–ray System", *Digiray Marketing Brochure,* at least by Dec., 1992, pp. 1–2.

Thomas S. Curry, III, et al., "Christensen's Physics of Diagnostic Radiology," pp. 1–522, Fourth Ed., Lea & Febiger, 1990.

X-RAY DETECTOR

CROSS-REFERENCE TO RELATED APPLICATIONS

This application is a continuation-in-part of U.S. patent application Ser. No.08/375,501, now abandoned filed Jan. 17, 1995, which is a continuation of U.S. patent application Ser. No. 08/042,742, filed Apr. 5, 1993, now abandoned; and, of International Pat. Application Ser. No. PCT/US94/03737, filed Apr. 5, 1994, which designated the United States from which priority is claimed under the provisions of 35 U.S.C. §§120 and 365, all of which are incorporated herein by reference in their entirety. The reader is referred to copending U.S. patent application Ser. No. 08/368,884 and copending U.S. patent application Ser. No. 08/386,861 both filed Feb. 10, 1995 concurrently with this application, the disclosures of which are incorporated herein by reference in their entirety.

BACKGROUND OF THE INVENTION

1. Field of the Invention

The present invention pertains generally to the field of radiation imaging. More specifically, the present invention pertains to the field of detectors for scanning beam x-ray imaging systems.

2. Description of Related Art

Real-time x-ray imaging is increasingly being required by medical procedures as therapeutic technologies advance. For example, many electro-physiologic cardiac procedures, peripheral vascular procedures, PTCA procedures (percutaneous transluminal catheter angioplasty), urological procedures, and orthopedic procedures rely on real-time x-ray imaging. In addition, modern medical procedures often require the use of instruments, such as catheters, that are inserted into the human body. These medical procedures often require the ability to discern the exact location of instruments that are inserted within the human body, often in conjunction with an accurate image of the surrounding body through the use of x-ray imaging.

A number of real-time x-ray imaging systems are known. These include fluoroscope-based systems where x-rays are projected into an object to be x-rayed and shadows caused by relatively x-ray opaque matter within the object are displayed on the fluoroscope located on the opposite side of the object from the x-ray source. An example of a known fluoroscopy system is U.S. Pat. No. 2,730,566 issued to Bartow, et. al. entitled "Method and Apparatus for X-Ray Fluoroscopy."

Reverse-geometry scanning-beam x-ray imaging systems are also known. In such systems, an x-ray tube generates an electron beam which is focussed upon a small spot on the relatively large anode (transmission target) of the tube, inducing x-ray radiation emission from that spot. The electron beam is deflected (electromagnetically or electrostatically) in a scanning pattern over the anode. A small x-ray detector is placed at a distance from the anode of the x-ray tube. The detector typically converts x-rays which strike it into an electrical signal in proportion to the detected x-ray flux. When an object is placed between the x-ray tube and the detector, x-rays are attenuated by the object in proportion to the x-ray density of the object. While the x-ray tube is in the scanning mode, the signal from the detector is inversely proportional to the x-ray density of the object.

The spatial resolution and the signal-to-noise ratio of x-ray images formed by known reverse-geometry scanning x-ray imaging systems are dependent, to a large extent, upon the size of the sensitive area of the detector. If the detector aperture is increased in area, more of the diverging rays are detected, effectively increasing sensitivity and improving the signal-to-noise ratio. At the same time, however, the larger detector aperture reduces attainable spatial resolution as the "pixel" size (measured at the plane of the object to be imaged) becomes larger. This is necessarily so because most objects to be imaged in medical applications (e.g., structures internal to the human body) are some distance from the x-ray source. In the known systems, therefore, the detector aperture size has been selected so as to effect a compromise between resolution and sensitivity, it not being previously possible to maximize both resolution and sensitivity simultaneously.

Examples of known reverse-geometry scanning-beam x-ray systems include those described in U.S. Pat. No. 3,949,229 to Albert; U.S. Pat. No. 4,032,787 to Albert; U.S. Pat. No. 4,057,745 to Albert; U.S. Pat. No. 4,144,457 to Albert; U.S. Pat. No. 4,149,076 to Albert; U.S. Pat. No. 4,196,351 to Albert; U.S. Pat. No. 4,259,582 to Albert; U.S. Pat. No. 4,259,583 to Albert; U.S. Pat. No. 4,288,697 to Albert; U.S. Pat. No. 4,321,473 to Albert; U.S. Pat. No. 4,323,779 to Albert; U.S. Pat. No. 4,465,540 to Albert; U.S. Pat. No. 4,519,092 to Albert; and U.S. Pat. No. 4,730,350 to Albert.

Accordingly there is a need for an x-ray detector which contains a large enough detection area to provide high detection sensitivity while containing sufficiently sized detection elements to maintain increased spatial resolution.

SUMMARY OF THE INVENTION

The detector of the present invention comprises a plurality of densely packed x-ray detectors preferably arranged into an array. Each detector preferably comprises a scintillator element which is optically coupled to a photodetector element, preferably with a fiber optic link. The detector array preferably includes integral alignment means to align the scintillator elements with the photodetector elements. The scintillator array elements are preferably formed from materials which possess a fast response and a minimum afterglow time.

These and many other objects and advantages of the present invention will become apparent to those of ordinary skill in the art from a consideration of the drawings and the description of the invention contained herein. The principles of the present invention may be employed in any application, medical or industrial.

DESCRIPTION OF THE PREFERRED EMBODIMENTS

Figure 1:
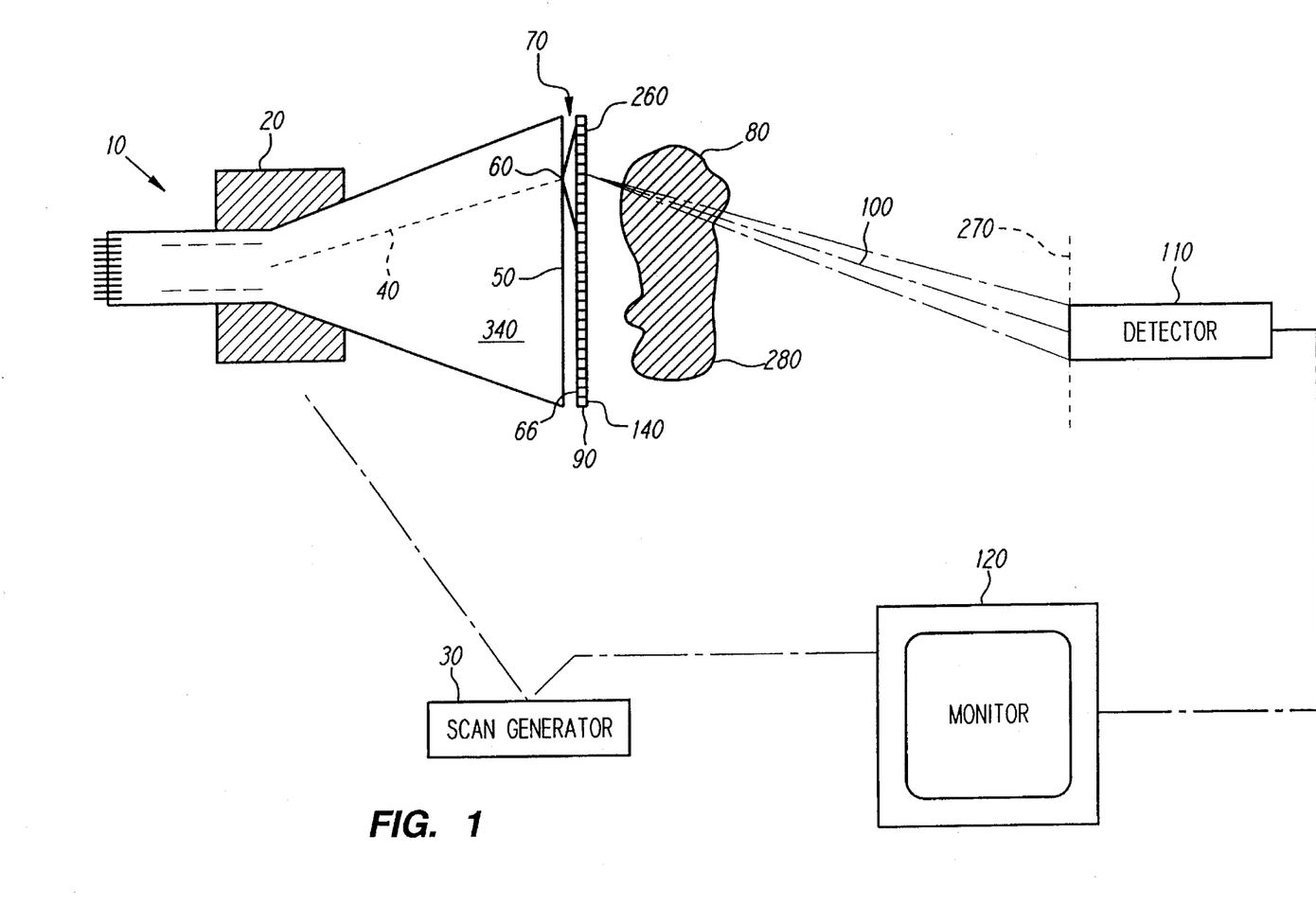
FIG. 1 is a diagram showing the basic components of a preferred scanning-beam x-ray imaging system.

Turning to FIG. 1, an embodiment of a presently preferred multi-detector array 110 employed in a reverse geometry scanning-beam x-ray imaging system is diagrammed. The preferred x-ray source 10, preferably a scanning beam x-ray tube, is more fully described in copending patent application Ser. No. 08/386,884, which has been incorporated herein by reference in its entirety. An electron beam 40 generated within x-ray source 10 is scanned across a grounded anode target 50 within x-ray source 10 in a predetermined pattern. For example, the predetermined pattern may be a raster scan pattern, a serpentine (or "S" shaped) pattern, a spiral pattern, a random pattern, a gaussian distribution pattern centered on a predetermined point of the anode target, or such other pattern as may be useful to the task at hand.

As electron beam 40 strikes anode target 50 at point 60, a cascade of x-rays 70 is emitted and travel outside of x-ray source 10 toward the object 80 to be investigated. To optimize system performance of the presently preferred embodiment, a cone of x-ray photons should be generated that will diverge in a manner that will just cover the multi-detector array 110.

This is preferably accomplished by placing a collimation grid 90 between the anode target 50 of the scanning x-ray source 10 and the multi-detector array 110, and more preferably between the anode target 50 and the object 80 to be imaged. Collimation grid 90, containing a grid of x-ray transmissive apertures 140, is designed to permit passage of only those x-ray pencil beams 100 whose axes lie in a path that directly intercepts multi-detector array 110. Thus, as electron beam 40 is scanned across anode target 50, at any given moment there is only a single x-ray pencil beam 100 which passes through object 80 to multi-detector array 110. The preferred collimation grid is described more fully in copending U.S. patent application Ser. No. 08/386,861, which has been incorporated herein by reference in its entirety.

The output of multi-detector array 110 is processed and displayed on monitor 120 as luminance values. Image processing techniques can be used to produce a computer driven image on an appropriate display or photographic or other medium. The preferred image processing techniques are described more fully in copending patent application Ser. No. 08/386,861, which has been incorporated herein by reference in its entirety.

To achieve resolutions of several line pairs per millimeter or more at the object plane, as are required in some medical applications, the spatial resolution limit in known x-ray imaging systems, particularly reverse-geometry systems, is in large part determined by the size of the single non-segmented detector. Generally speaking, a small non-segmented detector can provide high spatial resolution while a large non-segmented detector provides high collection efficiency. It has in part been this trade off that has been a problem in developing low dosage x-ray imaging systems.

By fabricating a multi-detector array 110 having a large area subdivided into multiple smaller detector array elements, a large capture area is achieved, and when using the image reconstruction methods described in copending U.S. patent Ser. No. 08/386,861, which has been incorporated herein by reference in its entirety, simultaneously retaining an image resolution that is comparable to the size of a single small detector element without increasing x-ray intensity an/or exposure time.

The preferred detector element employs a scintillator to convert x-ray photon energy to light energy. The light energy is then detected and converted to an electrical signal by means of a photomultiplier, photo diode, CCD or similar device.

The scintillator used to detect the x-ray photons preferably has the highest possible detective quantum efficiency. To achieve this, the scintillating material used in the individual detector elements preferably has a length in the direction in which the x-ray photons travel that is sufficient to ensure that no x-ray photons emerge from the end opposite the incident x-rays, i.e., the x-ray photon energy should be adequately dissipated in the material to maximize the output of the detector.

In the preferred x-ray imaging system in which the multi-detector 110 is used, which is described more fully in copending U.S. patent application Ser. No. 08/386,861, which has been incorporated herein by reference in its entirety, image information must be obtained in a very short time period, therefore the preferred detector element comprises a scintillator which has a fast response and a minimum afterglow time. Afterglow is the phenomenon wherein the scintillator continues to emit light after the stimulating incident x-rays have ceased.

Plastic scintillators, such as organic loaded polystyrene, are suitable from a standpoint of speed in that they have the required fast response and minimum afterglow characteristics. However, plastic scintillators have a relatively small x-ray photon interaction cross section so that their linear x-ray absorption coefficients are also small in value. The consequence is that a considerable thickness is required to absorb x-ray photons. For 100 keV x-rays, a typical plastic scintillator should be about 28 cm (11 in) thick to capture 99% of the incident x-rays.

The preferred scintillator materials are: (1) YSO (cerium doped yttrium oxyorthosilicate) (2) LSO (cerium doped lutetium oxyorthosilicate) and (3) BGO (bismuth germanate). All three are available from Airtron (Litton Industries) of Charlotte, N.C. YSO and LSO are the preferred materials with YSO more preferred on the basis of cost. LSO has a higher stopping power for x-rays so it is the first preference for use with higher voltage x-ray sources, since a length shorter than that of YSO can be employed to stop x-rays of similar energies. BGO must be heated to about 100° C. in order to achieve the required light output decay period of about 50 nanoseconds. These scintillators typically provide high quantum efficiencies. For 100 keV x-rays, the preferred length for YSO is 0.5 cm.

According to a presently preferred embodiment, the scintillators are coated on 5 sides with aluminum which is preferably applied by evaporation in vacuo. The uncoated side is that from which the scintillation light emerges to a light detector. In an alternative embodiment, the scintillators are coated on 5 sides with titanium dioxide paint. In both these embodiments, the coatings reflect the scintillation light internally within the scintillator crystal so that it is prevented from escaping except from the uncoated side thus providing a high light transfer efficiency to the light detector means which is optically coupled to the uncoated side.

Figure 2:
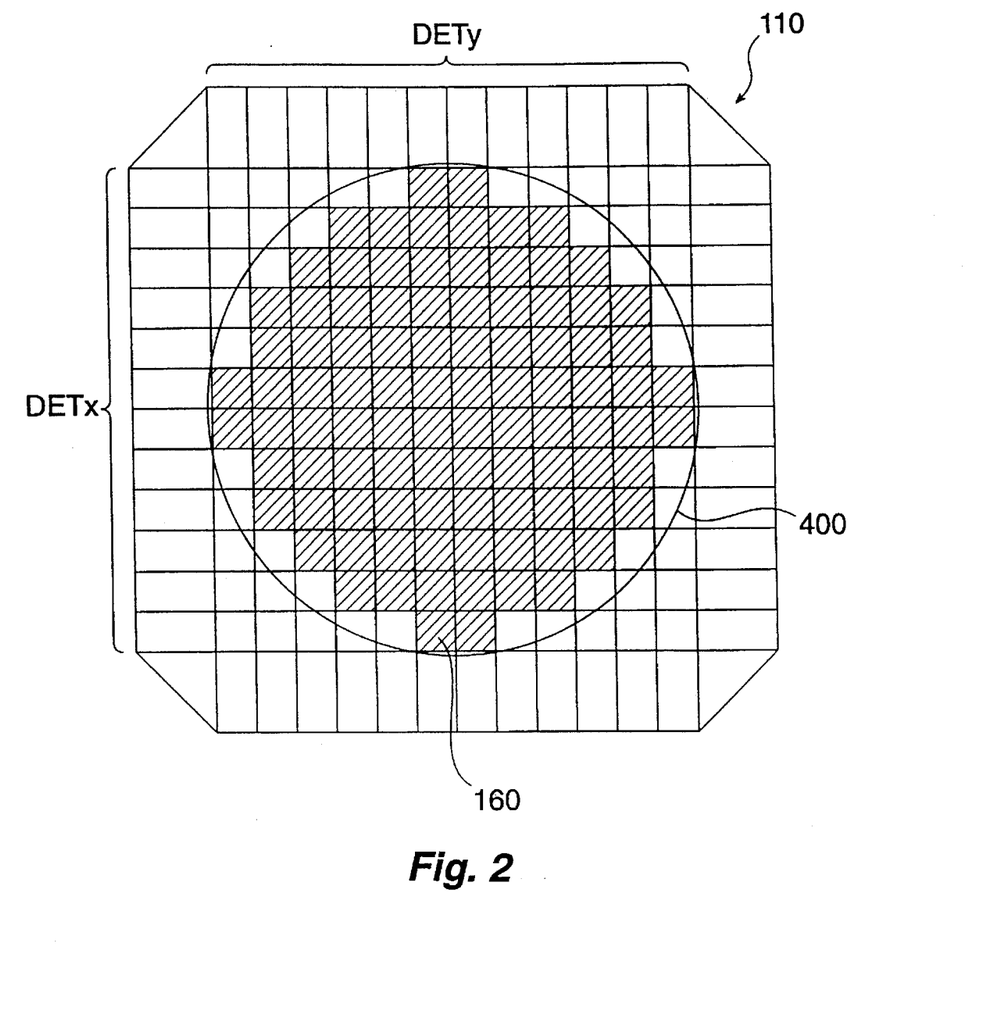
FIG. 2 is a diagram of the preferred arrangement of 96 scintillator elements to form a pseudo-circular array.

According to one embodiment of the present invention, multi-detector array 110 comprises at its input face a pseudo-round array of 96 densely packed scintillators including two rows of 12 and two columns of 12 at its horizontal and vertical midplanes (FIG. 2). A square 5-by-5 and a square 3-by-3 array are also contemplated as is a non-square array of scintillators filling a circle about the center of the multi-detector array.

Figure 3:
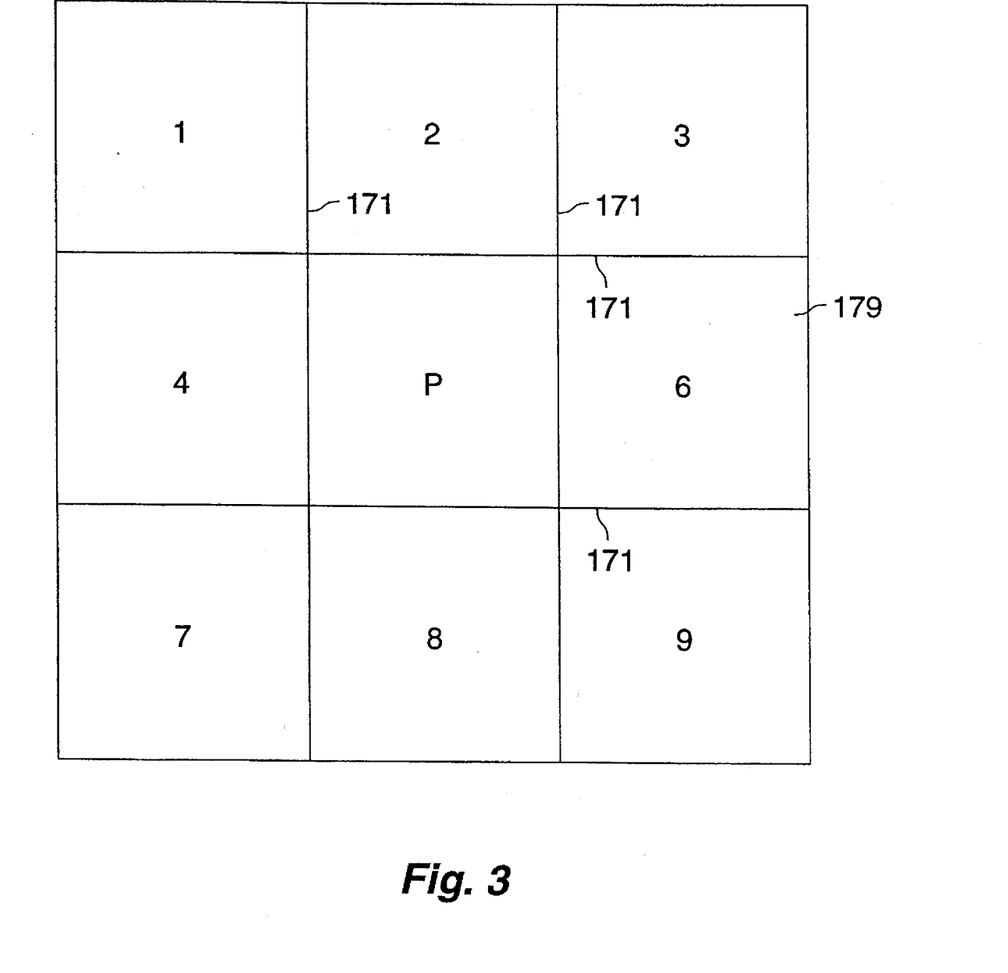
FIG. 3 is a diagram of a 3×3 multi-detector array.

X-ray photons striking any one scintillator 170 should contribute to the final x-ray image with the spatial position reference that corresponds to the position of that one scintillator only. Light or x-rays striking a scintillator which couples into adjacent scintillators may cause a degradation of image quality. Such cross-talk between scintillators can be caused by some or all of the following mechanisms: direct light transmission, scattered incident x-rays, x-rays entering near to the scintillator edge which have an angle of incidence greater than zero and fluorescent x-rays generated within the scintillator material. This problem is preferably addressed by placing septa 171 between neighboring scintillators which are made out of a material which is opaque to light and which greatly attenuates x-rays. An example of a preferred positioning of septa 171 is shown in FIG. 3. While the x-ray collection efficiency may be reduced by the finite thickness of septa 171, which will intercept some x-ray photons, the quality of the final x-ray image is not affected to any substantial degree. Preferred materials for septa 171 are those with a high atomic number such as gold, platinum, tantalum, tungsten or lead. In the preferred embodiment described in detail later, the septum material is tungsten loaded epoxy. The thickness of septa 171 is preferably in the range 0.005 cm (0.002") to 0,013 cm (0,005"). The choice of thickness and material for septa 171 is dependant to some degree on the choice of scintillator material. The predominant fluorescent x-rays from YSO are emitted with an energy of about 15 keV and will be adequately stopped by septa at the low end of the quoted thickness range whereas the predominant x-rays from LSO have an energy of about 54 keV and a greater septum thickness will be required.

Figure 4:
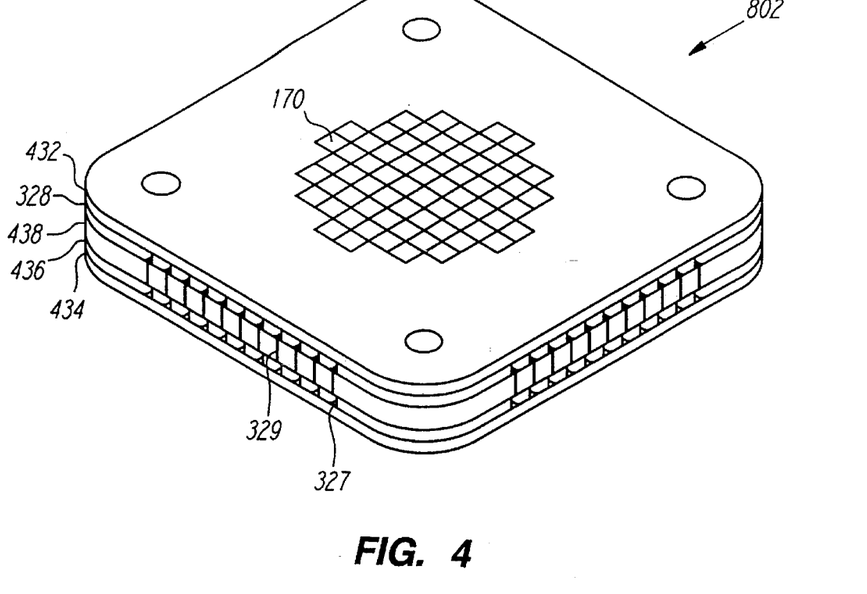
FIG. 4 is an orthogonal view of a preferred scintillator assembly.
Figure 5:
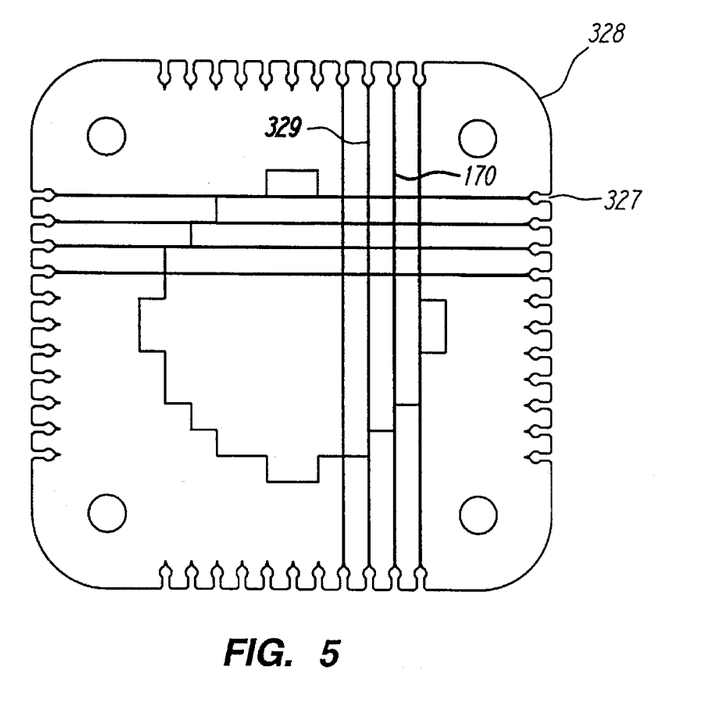
FIG. 5 diagrams a preferred wireframe for the scintillator assembly of FIG. 4.

FIG. 4 is a representation of the preferred scintillator assembly 802 comprising a scintillator array 112, end-plates 432 and 434, wireframes 328 and 436, and spacer 438. Wireframe 328, best shown in FIG. 5, is preferably a sheet of stainless steel which measure approximately 1,125 inches on each side. A pseudo-circular pattern with a diameter of approximately 0.719 inches is cut in the center of wireframe 328. Eleven notches 327, approximately 0.06 inches in depth, are evenly spaced along the center 0.60 in. section on each edge of wireframe 328. Wireframe 436 is identical to top wireframe 328.

To construct the scintillator assembly 802, a spacer 438 is disposed between wireframes 328 and 436. Spacer 438 is preferably a flat piece of metal with a circular opening in its center corresponding to the circle defined by the scintillator array 112. Wires 329 are stretched from a notch 327 on one edge of wireframe 328 to the notch on its directly opposite edge, and then are wrapped around the spacer 438 to the corresponding notches on wireframe 436. When a wire 329 has been stretched through every notch 327 on both wireframes, 96 square sections will be created in the pseudo-circular hole that was formed in wireframes 328 and 436.

An x-ray sensitive scintillator element 170 is placed into each of these square sections within the wireframe arrangement to form the scintillator array 112. The scintillator elements 170 are preferably cut to a square horizontal cross-section. The length of the individual scintillator elements 170 are preferably about 0.5 cm and the exterior faces are preferably 0.135 cm×0.135 cm. The scintillator elements 170 are preferably YSO, but other materials may also be used as discussed above. The stretched wires 329 help to align the placement of the scintillator elements 170. A composition of tungsten loaded epoxy is preferably used to fill the space between and around the scintillator elements 170 and to fill the gaps created by the wires 329 when stretched across the wireframes 328 and 436.

In another embodiment, a frame equal in depth to the scintillator length and preferably 1.25" square incorporates integral septa to form preferably 96 square section holes into which the scintillators are inserted and held in place by means of preferably epoxy adhesive. The frame is preferably made by the electrical discharge machining process. In another embodiment the aforementioned frame is built up out of thin lamina which incorporate preferably 96 square section holes. Each lamination would be preferably 0.05 cm thick and would be made by a chemical etching process. In yet another embodiment, the aforementioned frame is machined with a pseudo-circular hole and with two 90° sets of milled slots in its edges, each slot preferably slightly wider than the septum material thickness and spaced apart by a distance equal to the scintillator spacing. Strips of septum material preferably equal in width to the scintillator length and preferably 1.00" long are inserted into the milled slots to form the septa. Each strip of septum material preferably has slots, slightly wider than the material thickness, which are spaced apart by a distance equal to the scintillator spacing and which extend half way across the strip width. The x-axis strips consequently mesh with the y-axis strips in the manner of an egg crate to form 96 square section holes into which the scintillators are inserted and secured by preferably epoxy adhesive.

In the preferred embodiment the output face of the scintillator assembly 802 is lapped to produce a flat polished surface after insertion of scintillators elements 170.

Figure 6:
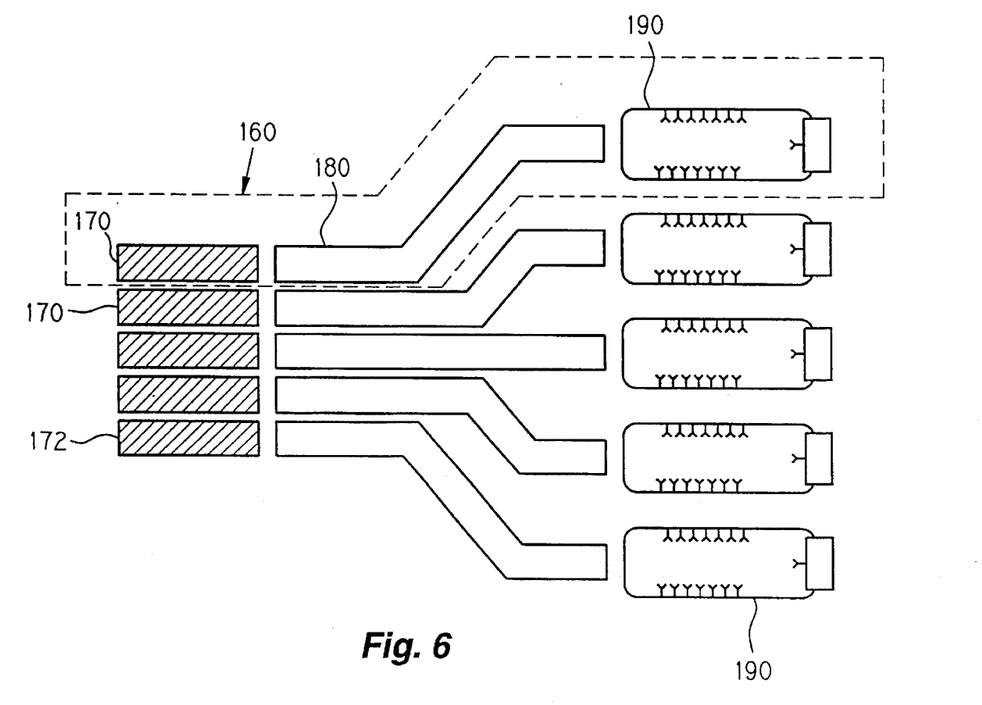
FIG. 6 is a functional representation of one row or column of detector elements for a 5×5 multi-detector array.

According to one presently preferred embodiment of the detector element 160 (FIG. 6), each scintillator element 170 is preferably in contact with a light pipe or fiber optic link 180 which optically couples each scintillator element 170 with a corresponding photomultiplier tube channel 190 or solid state detector. A suitable coupling medium is preferably applied between each end of the fiber optic link 180 to ensure low transmission losses at the interfaces.

Figure 7:
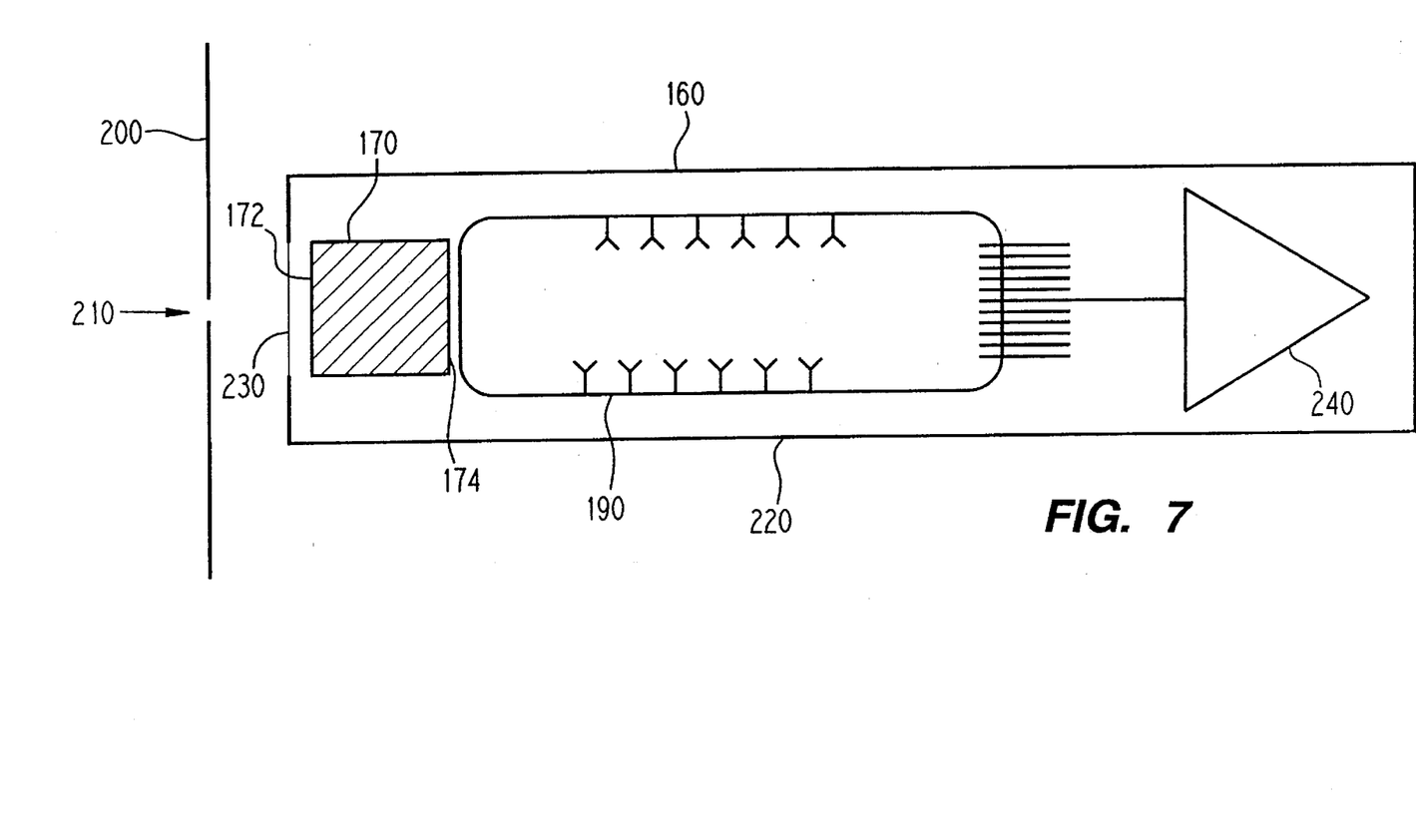
FIG. 7 depicts one embodiment of a detector element.

Alternatively, scintillators 170 may be located in close physical proximity to their corresponding photodetectors, as shown in FIG. 7, eliminating the need for a fiber optic link. In the embodiment shown in FIG. 7, an x-ray opaque sheet 200 with apertures 210 corresponding to each detector element 160 is disposed in front of multi-detector array 110. Each detector element 160 is enclosed in a light tight enclosure 220 which may also be x-ray opaque. A light blocking window 230, preferably made of a thin aluminum sheet, is located at the front of light tight enclosure 220. Light blocking window 230 is x-ray transmissive. Within light tight enclosure 220 is a scintillator element 170 in close proximity to a photomultiplier tube 190 which is preferably electrically connected to a pre-amplifier 240.

Alternatively the scintillator array can be placed in direct or close contact with an array of photo diodes, avalanche photo diodes, vacuum avalanche photo diodes, photo transistors or charge coupled devices to achieve a rugged and compact detector. Where solid state devices, particularly CCDs, are used, cooling, such as with a Peltier-type cooler, or the like, may be employed to increase the signal-to-noise ratio of the device. Alternatively the scintillator array could be coupled optically or be in direct or close contact with one or more position sensitive optical detectors, preferably a multi-channel photomultiplier tube or a segmented anode microchannel plate image intensifier, which provide an output signal which identifies the position coordinates of the light source as well as its amplitude.

Figure 8:
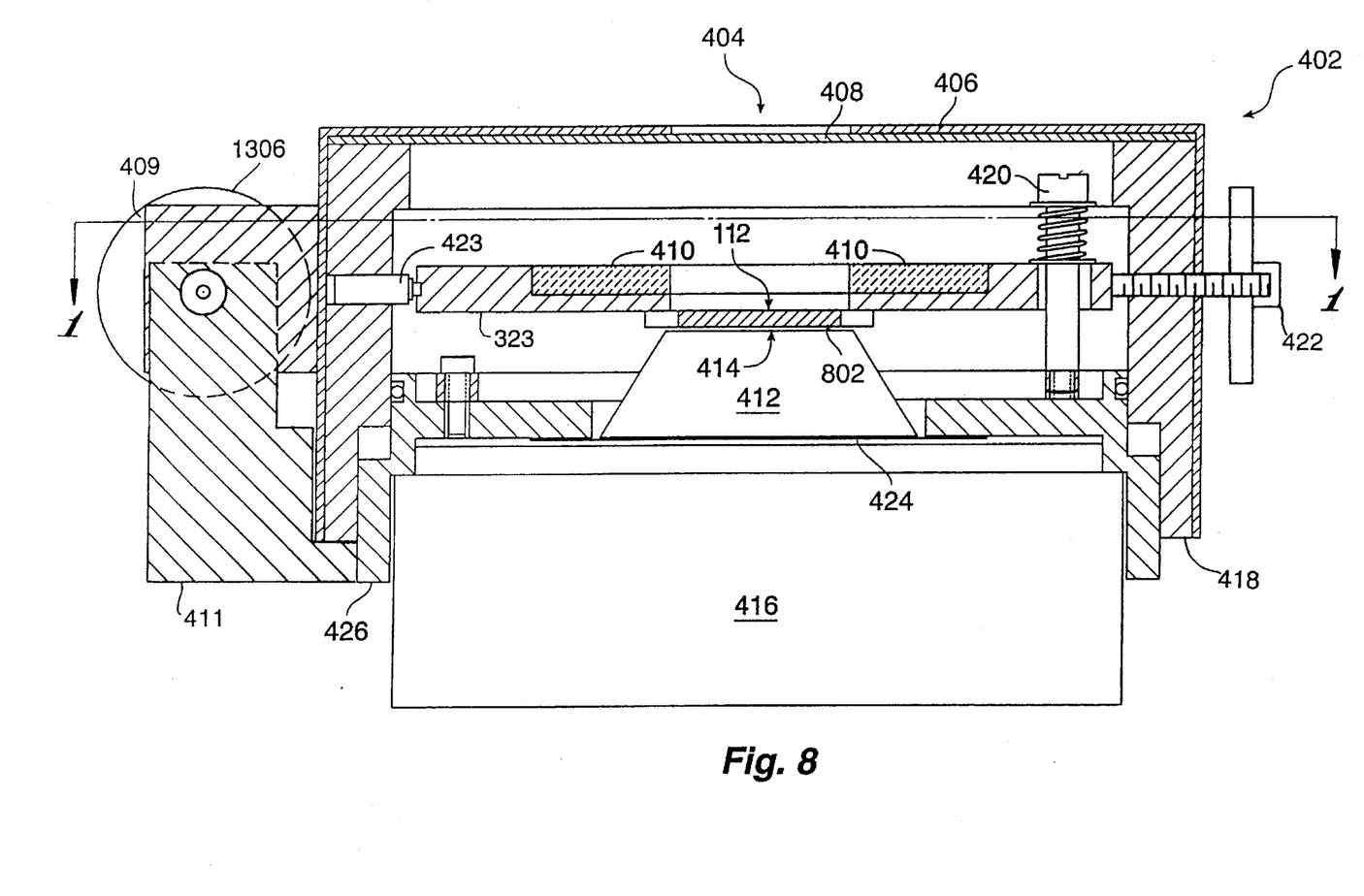
FIG. 8 is a partial cross-sectional representation of one embodiment of a multi-detector array assembly.

Referring to FIG. 8, one embodiment of a multi-detector array assembly 402 comprises a scintillator assembly 802, a multi-channel photomultiplier tube 416, a fiber optic link 412, integral alignment means, and an outer detector housing 418. Multi-detector array assembly 402 preferably contains a light tight outer detector housing 418 to minimize any noise which may be generated by stray light. X-rays enter the multi-detector array assembly 402 through an x-ray window 404 in lead shield 406. X-ray window 404 is preferably circular and about 1.91 cm (0.75 in) in diameter to permit a directed beam of x-rays to strike the scintillator array 112 while attenuating scattered x-rays. A light shield 408 is preferably employed to shield the assembly from ambient light. The light shield 408 may be made of a thin sheet of aluminum or beryllium chosen to attenuate light without substantially attenuating the x-rays, and is preferably 0.0125 cm thick.

Figure 9:
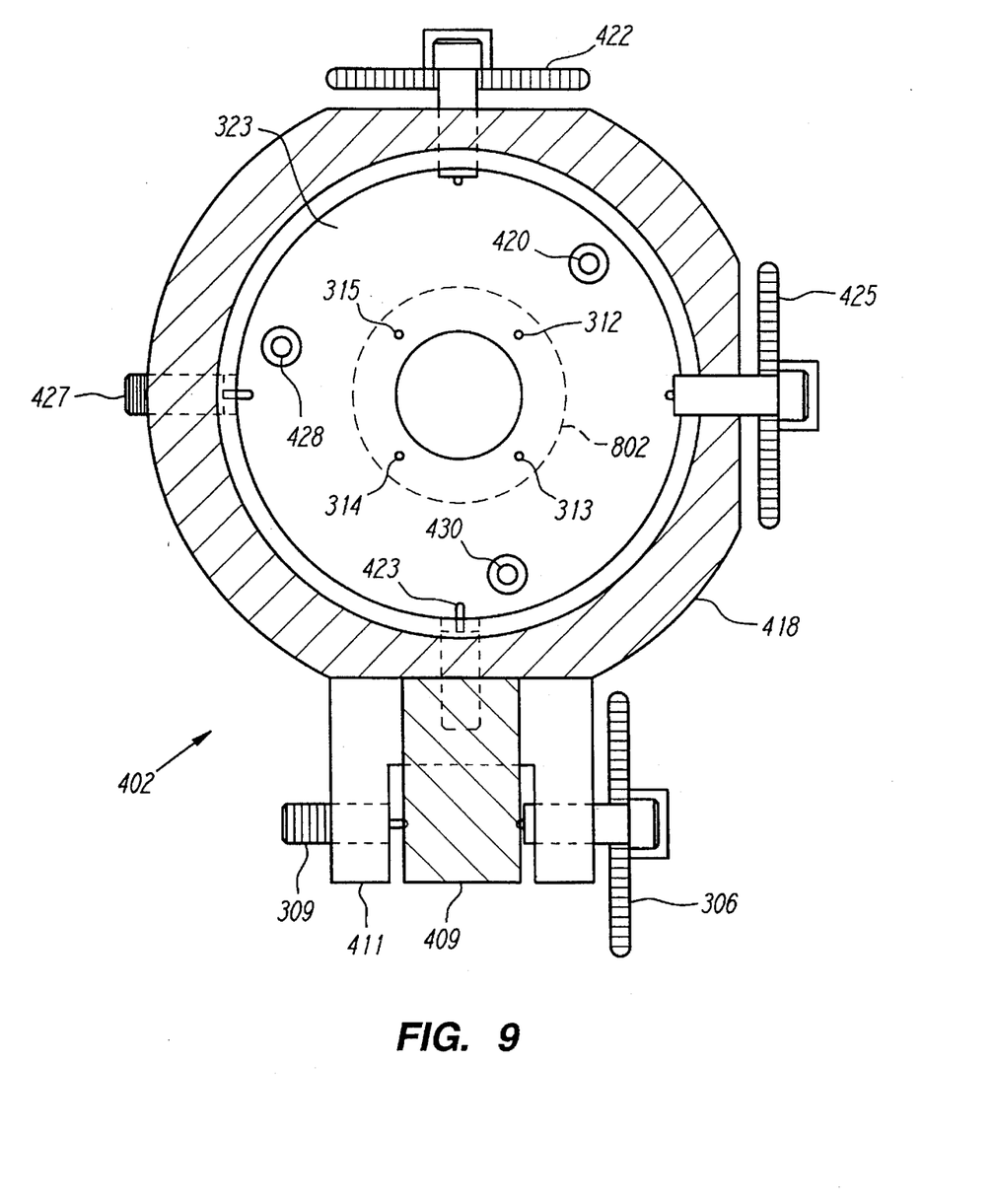
FIG. 9 is a top view representation taken along plane 1—1 of the multi-detector array assembly of FIG. 8.

Scintillator assembly 802 is preferably positioned such that the pseudo-circular scintillator array 112 is substantially aligned with the x-ray window 404. As shown in FIG. 9, scintillator assembly 802, which is outlined in phantom, is preferably attached to adjuster plate 323 with attachment screws 312, 313, 314 and 315. If BGO scintillators are employed, then a heating element 410, preferably a resistive heating element designed to keep the scintillator assembly 820 at an operating temperature of about 100° C., is positioned on the adjuster plate 323. The preferred scintillator assembly 802 is described more fully in connection with the detailed description of FIGS. 4 and 5.

An optical link, preferably a fiber optic imaging taper 412, directs light photons emerging out of the bottom 414 of the scintillator assembly 802 to a multi-channel photomultiplier tube (PMT) 416. The preferred fiber optic imaging taper 412 is available from Collimated Holes of Campbell, Calif. and has a circular input aperture diameter of approximately 2.03 cm (0.8 in) and a circular output aperture diameter of approximately 3.38 cm (1.33 in). Fiber optic imaging taper 412 matches each scintillator crystal pitch dimension (0.06") to that of the PMT 416(0.10"), i.e., it has a magnification of 1,667 times. High viscosity optical coupling fluid available from Dow Corning (Type 200) with a refractive index approximately matching that of the glass may be used at the two faces of the taper as an optical coupling medium to maximize the light transfer efficiency from the scintillator crystals 170 to the fiber optic imaging taper 412 and from the fiber optic imaging taper 412 to the PMT input face 424.

Figure 10:
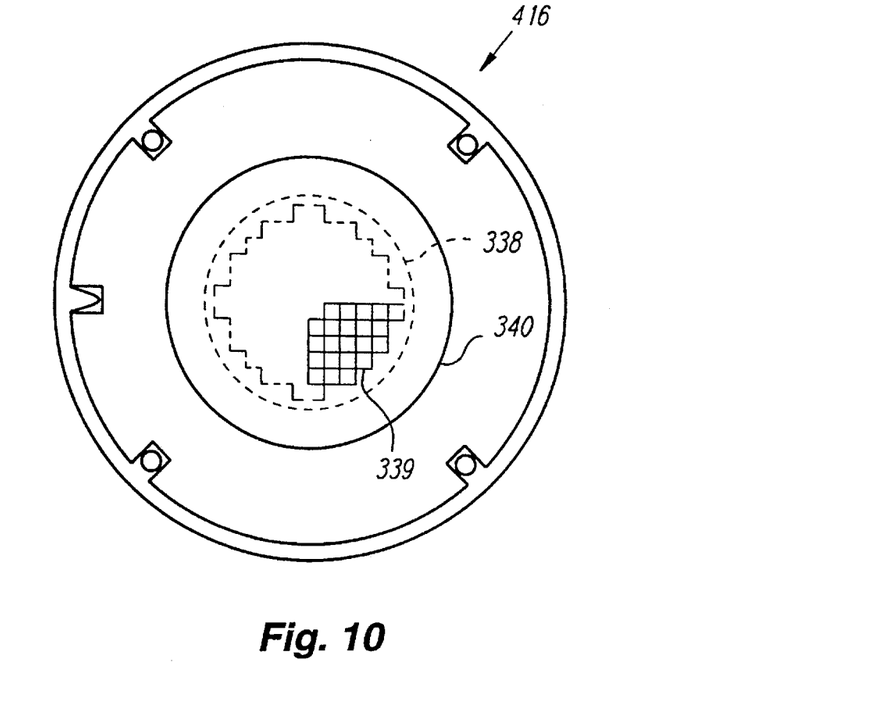
FIG. 10 is a top view of a preferred 96-channel photomultiplier tube.
Figure 11:
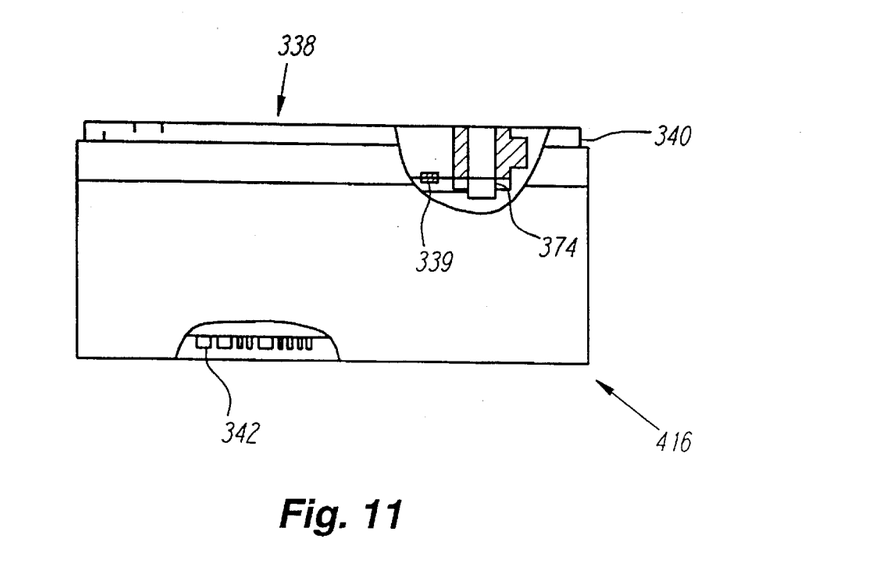
FIG. 11 is a partial cross-sectional side view of the photomultiplier tube of FIG. 10.

The preferred PMT 416 is a 96-channel tube (one channel corresponding to each scintillator crystal 170) model number XP 1724A available from the Philips Corporation. As shown in FIGS. 10 and 11, it preferably has a fiber optic face plate 340 so that the spatial arrangement of the scintillator array 112 is accurately carried through to the PMT photocathode located in the PMT on the other face of the faceplate. 96 photocathode elements 339 are arranged in a pseudo-circular array in the center of the front face of PMT 416. Each photocathode element is preferably square in shape with dimensions of 2.54 mm×2.54 mm. An x-ray photon striking one of the scintillators 170 produces many light photons, some of which are coupled to the PMT photocathode. This produces a corresponding electron pulse at the photocathode and the pulse is amplified in one channel of the PMT dynode structure up to approximately 1,000,000 times.

The pseudo-circular array of 96 photocathode elements creates a light-sensitive circular area 338 on the PMT 416 with a diameter of 30.5 mm. It is this light sensitive area 338 that interfaces with the tapered fiber optic bundle 412. Each PMT photocathode element 339 has a corresponding electrical output connector 342. When light photons reach the PMT 416, the photocathode elements 339 generates signals which are amplified by the dynode structure and output at PMT connectors 342.

Referring again to FIG. 9, three positioning screws 306, 422, and 425 are provided for linear and rotational alignment of the scintillator assembly 802 relative to the PMT 416. Adjuster plate 323 is attached to PMT mount 426 with three shoulder screws 420, 428, and 430 through alignment holes with diameters larger than the diameter of the shoulder screws. Shoulder screws 420, 428, and 430 are spring loaded (shown in FIG. 8) so that adjuster plate 323 is fixed because of the tension applied by the shoulder screw springs, but can be further manipulated for positioning purposes.

Attached to the side of detector housing 418 is y-axis positioning screw 422. Spring loaded return pin 423 is located on the side of detector housing 418 directly opposite y-axis positioning screw 422 and biasing the adjuster plate against the y-axis positioning screw 422. Rotation of y-axis positioning screw 422 will move the adjuster plate 323 along the y-axis, causing a corresponding shift in the y-axis position of the attached scintillator array 112. Similarly, x-axis positioning screw 425 and spring loaded return pin 427 operate in an identical manner to adjust the x-axis positioning of the scintillator array 112.

To adjust the rotational positioning of the scintillator array 112, a tongue 409 of outer detector housing 418 is positioned between rotational positioning screw 306 and spring loaded return pin 309. The tongue 409 is placed between the ends of rotational bracket 411, and is biased by the tension of the loaded return pin 309 against rotational positioning screw 306. Adjusting the rotational positioning screw 306 will cause a rotational shift in the tongue 409 of the outer detector housing 418, causing a corresponding shift in the attached adjuster plate 323, which results in an adjustment of the scintillator array 112 with respect to the PMT 416.

Figure 12:
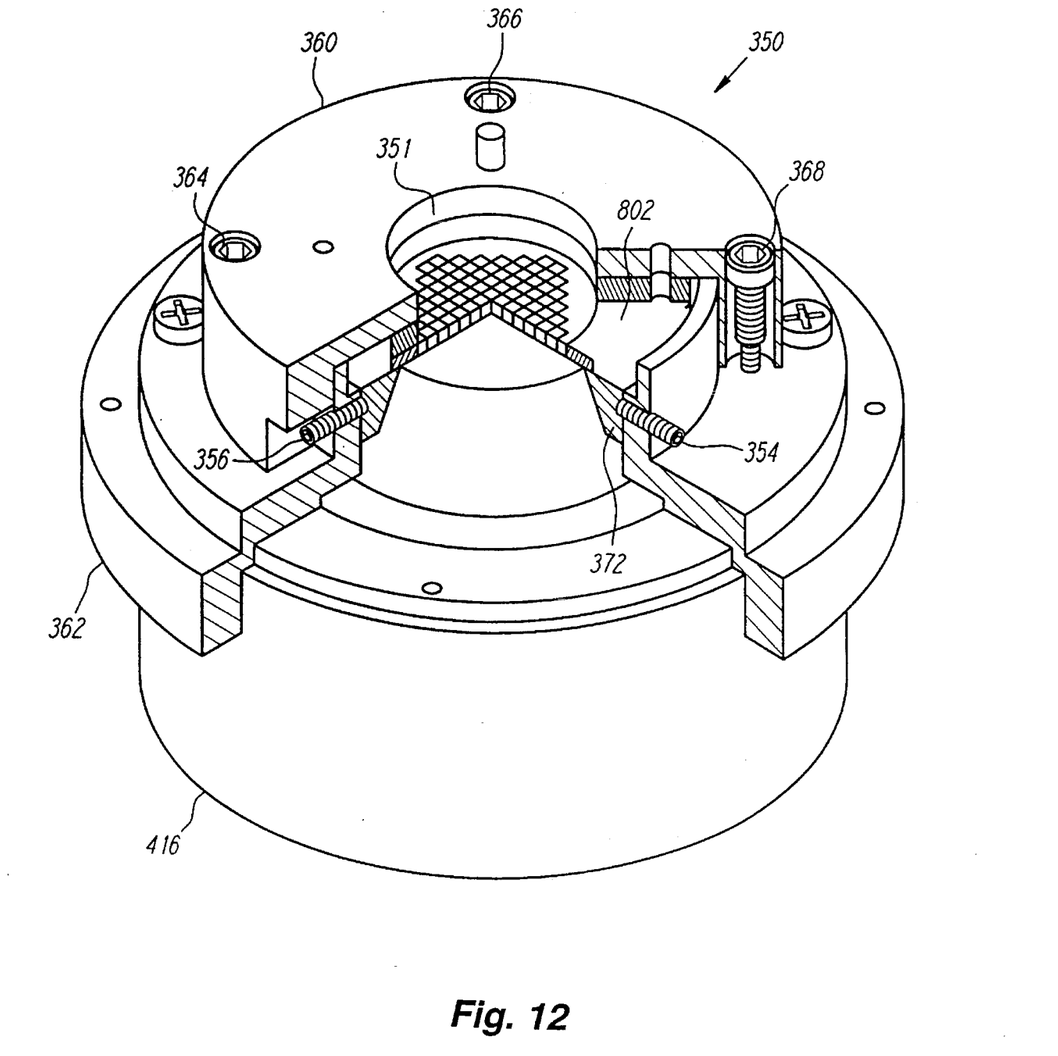
FIG. 12 is a partial cross-sectional perspective view of another embodiment of a multi-detector array assembly.
Figure 13:
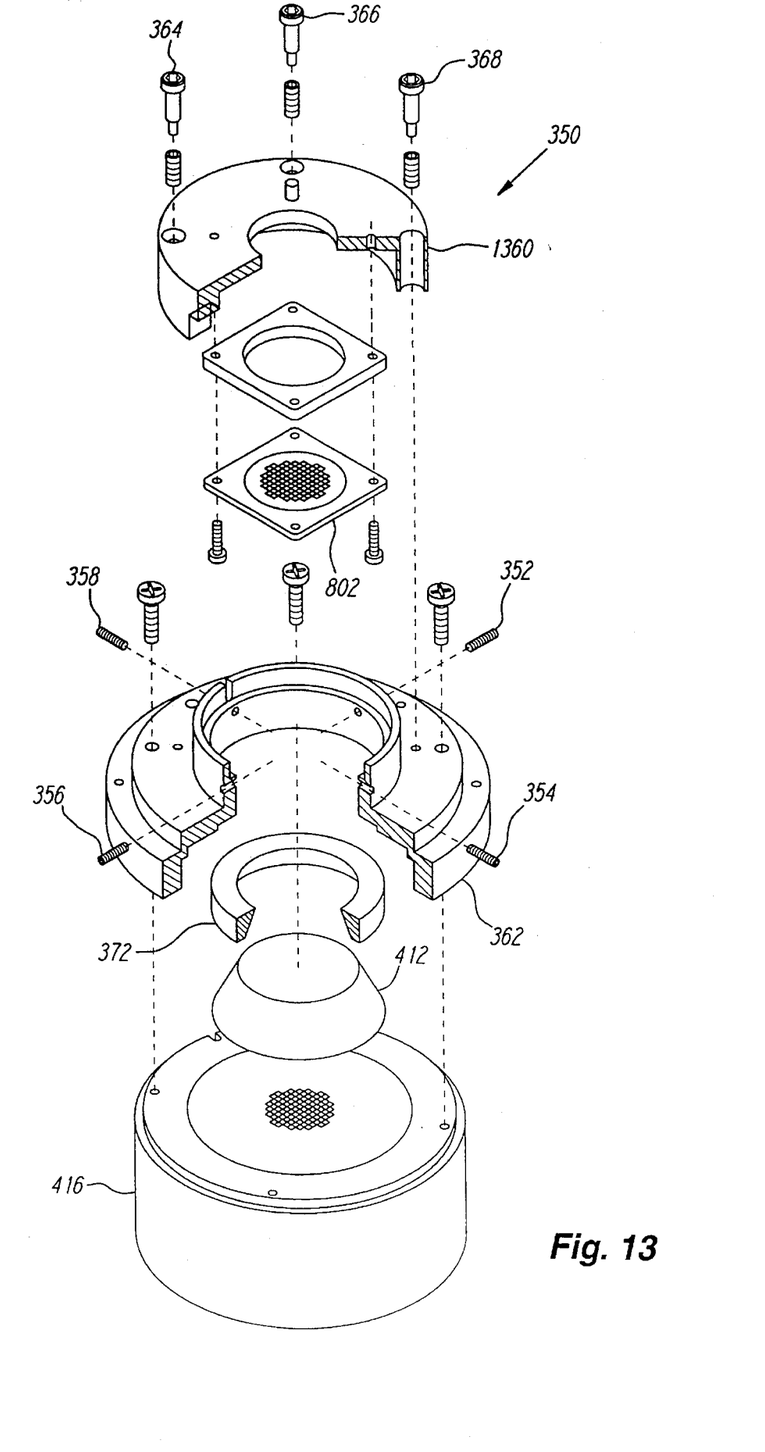
FIG. 13 is an exploded view of the multi-detector array assembly of FIG. 12.

Another embodiment of a multi-detector array assembly 350 depicted with alternate alignment means is shown in FIGS. 12 and 13. X-rays enter through a circular x-ray window 351, preferably 1.91 cm in diameter, which is located in an x-ray opaque detector housing 360. A light shield (not shown) can be disposed adjacent the x-ray window to shield the assembly from ambient light. A scintillator assembly 802, preferably the scintillator assembly described more fully in connection with the detailed description of FIGS. 4 and 5, is rigidly bolted to the interior surface of the detector housing 360. Detector housing 360, with the scintillator assembly 802 rigidly attached, is attached to the PMT mount 362 with four shoulder screws 364, 366, 368, and 370 (370 not shown) through alignment holes with diameters larger than the diameter of the shoulder screws.

Shoulder screws 364, 366, 368, and 370 are spring loaded so that detector housing 360 moves axially, because of the tension applied by the shoulder screw springs, to maintain the scintillator assembly 802 in contact with fiber optic imaging taper 412 and to maintain the fiber optic imaging taper 412 in contact with the input face of the PMT 416.

Adjustment collar 372, preferably formed with a cylindrical outer surface and a tapered inner surface, is positioned within the upper aperture of PMT mount 362. Fiber optic imaging taper 412, preferably inserted along the inner tapered surface of the adjustment collar 320, is mounted between the scintillator array 112 and the input face of the PMT 416. The preferred fiber optic imaging taper 412 was described more fully in connection with the detailed description of FIG. 8. PMT 416, preferably the photomultiplier tube described more fully in connection with the detailed description of FIGS. 10 and 11, is rigidly bolted into the lower stepped opening of PMT mount 312.

Four alignment screws 352, 354, 356, and 358 are preferably employed to align the fiber optic imaging taper 412 within the multi-detector array assembly 350. The alignment screws are disposed within four apertures equidistantly placed through the upper walls of the PMT mount 362. The alignment screws are positioned such that they form solid contact with the adjustment collar 372, which is yoked around the fiber optic imaging taper 412. A viscous silicon optical-coupling medium is applied along the two faces of the fiber optic imaging taper 412. To effect the alignment of the fiber optic imaging taper 412, alignment screws 352, 354, 356, and 358 are manipulated such that pressure is applied to the alignment collar 372 in the required alignment direction. This repositions the alignment collar 372, forming a corresponding repositioning of the fiber optic imaging taper 412.

Figure 14:
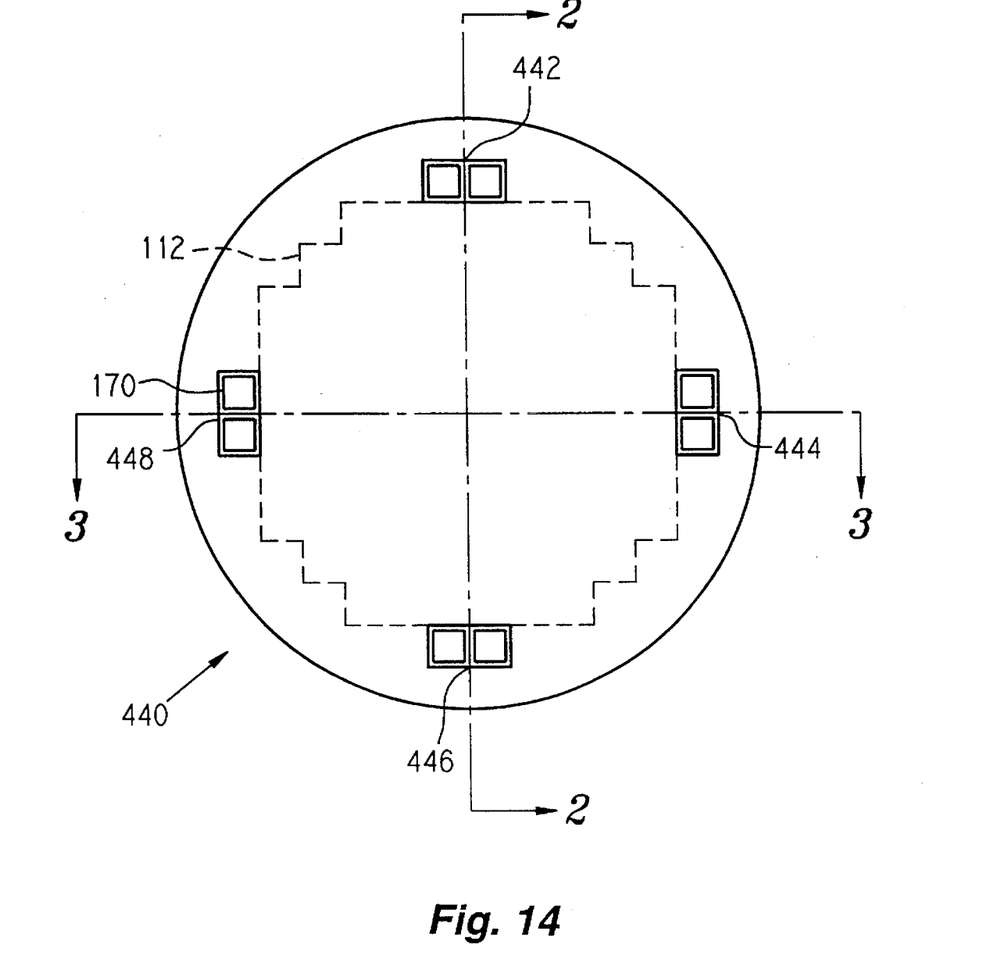
FIG. 14 is a top view of a preferred x-ray alignment shield.

According to one method to optimally align the scintillator elements 170 in relation to their corresponding photomultiplier tube elements 339, an x-ray shield 440, formed of an x-ray opaque material and containing x-ray transmissive windows, is disposed before the input face of the scintillator array 112. As shown in FIG. 14, the preferred x-ray shield 440 is a circular disc formed of lead with four equally sized x-ray transmissive windows (442, 444, 446, and 448), equidistantly spaced along the outer perimeter, such that each x-ray transmissive window corresponds to an equivalent number and placement of scintillator elements 170 along the outer edge of the preferred scintillator array 112 (outlined in dashed lines). For the purposes of the explanation below, the line 2—2 will be referred to as the y-axis and the line 3—3 will be referred to as the x-axis.

An x-ray source is positioned such that an even spread of x-rays is directed at the x-ray shield 440. Suitable measurement means are connected to the output leads of the PMT 416 to measure the electrical signals produced by the specific PMT channels which correspond to scintillator elements 170 located adjacent to the x-ray transmissive windows 442, 444, 446, and 448. Such measurement means may comprise, for example an amplifier and a comparator to count the number of light photons detected by the PMT 416, employing photon counting circuitry described more fully in copending patent application Ser. No. 08/386,861, which has been incorporated herein by reference in its entirety. Suitable means are preferably employed to amplify and balance the output signals from the PMT channels, as described more fully in copending U.S. patent application Ser. No. 08/386,861, which has been incorporated herein by reference in its entirety.

The alignment procedure is initiated by a directed emission of x-rays spread evenly across the face of the x-ray shield 440. If the scintillator elements are optimally aligned with their corresponding PMT channels along the y-axis, then the output signals from the PMT channels which correspond to the scintillator elements 170 adjacent to x-ray windows 442 and 446 should be maximized. To effect a y-axis alignment, the scintillator array 112 is positionally adjusted along the y-axis in the manner described more fully in connection with FIGS. 12 and 13, and after each adjustment, another directed emission of x-rays is evenly spread across the face of x-ray shield 440. This process repeats until maximum levels of output signals are measured for the PMT channels corresponding to the y-axis scintillator elements 170 adjacent x-ray windows 442 and 446. Similarly, the x-axis alignment process involves the manipulation of the scintillator array 112 along the x-axis, in the manner more fully described in connection with FIGS. 8–9, until further beams of x-rays directed at the x-ray shield 440 produce maximum levels of output signals measured for the PMT channels corresponding to the x-axis scintillator elements 170 adjacent x-ray windows 444 and 448.

Once the scintillator array 112 is optimally aligned along the x and y axes, the next step is to rotationally align the scintillator array 112. As with the x and y alignment, the process is initiated by an even spread of x-rays directed at the outer face of x-ray shield 440. When the scintillator array 112 is rotationally adjusted to the optimal positioning, then the level of visible light transferred to the PMT 416 should be at a maximum. Therefore, the scintillator array 112 is manipulated rotationally in the manner described in connection with FIGS. 8–9, and a directed beam of x-rays are emitted after each adjustment, until any further rotational manipulations would result in less visible light being detected by the PMT 416. If necessary, the y-axis and x-axis alignment procedures can be repeated after the rotational adjustments have been made to correct x or y-axis misalignments introduced by the rotational adjustments.

An alternate alignment method comprises the use of a high-power microscope to optimally align the scintillator elements 170 with their corresponding photomultiplier tube channels. According to this method, the input faces of the scintillator elements 170 are polished as well as the output faces. The multi-detector array assembly 350, is mounted to an alignment stand and a microscope is placed along the input face of the scintillator crystal array 112. To effect the optimal alignment, the microscope is initially positioned over the input face of one of the scintillator elements 170 along the outer perimeter of the scintillator array 112. The positioning screws within the multi-detector array 350 are manipulated, in the manner described in connection with FIG. 9, such that fiber optic imaging taper 412 is repositioned relative to the scintillator array 112. The positioning screws are manipulated until the photomultiplier tube channel corresponding to the observed scintillator element 170 is optically centered in relation to the scintillator element 170. The process is then repeated with another scintillator element 170 along the outer perimeter of the scintillator array 112 directly opposite the just aligned scintillator element 170. The above process is repeated until all the scintillator elements 170 along the outer perimeter of the scintillator array 112 are properly aligned.

While embodiments, applications and advantages of the invention have been shown and described with sufficient clarity to enable one skilled in the art to make and use the invention, it would be equally apparent to those skilled in the art that many more embodiments, applications and advantages are possible without deviating from the inventive concepts disclosed and described herein. The invention therefore should only be restricted in accordance with the spirit of the claims appended hereto and is not to be restricted by the preferred embodiments, specification or drawings.

What is claimed is:

1. An x-ray detector comprising a plurality of detector elements, said detector elements arranged in an array, said array comprising a plurality of rows and columns;

each of said detector elements comprising a scintillator element, an optical coupling element, and a photodetector element;

said scintillator element comprising a material which produces light photons when excited by x-ray photons;

said optical coupling element comprising an input face and an output face, said input face substantially adjacent said scintillator element, said output face substantially adjacent said photodetector element;

said photodetector element comprising a light photon detector and an electrical signal generator, said electrical signal generator outputs electrical signals in proportion to said light photons detected by said light detector;

a scintillator array assembly in which said scintillator elements are disposed, said scintillator array assembly comprising a top frame, a bottom frame, a top endplate, a bottom endplate, wires and a spacer;

said spacer comprising a plate with a central opening, said top frame and said bottom frame comprising a plurality of notches formed around the periphery of said frames and having a central opening corresponding to the array configuration;

said spacer disposed between said top frame and said bottom frame, said wires extending across said frames from corresponding notches on each edge of said top frame and said bottom frame forming an array of scintillator spaces, each of said scintillator elements disposed in said scintillator spaces, a septa material disposed between said scintillator elements, said top endplate disposed over said top frame, said bottom endplate disposed over said bottom frame.

2. A multi-detector assembly comprising a scintillator array assembly, a fiber optic taper, a multi-channel photomultiplier tube, and a multi-detector housing;

said scintillator array assembly comprising a plurality of scintillator elements, each of said scintillator elements comprising a material which produces light photons when x-ray photons strike said scintillator elements;

said multi-channel photomultiplier tube comprising a plurality of photodetector elements, each of said photodetector elements comprising a light detector and an electrical signal generator, said electrical signal generator outputs discrete electrical signals in response to said light photons detected by said light detector;

said fiber optic taper comprising a plurality of fiber optic cables, each of said fiber optic cables comprising an input face and an output face, said input face substantially adjacent said scintillator elements, said output face substantially adjacent said photodetector elements;

said multi-detector housing comprising an x-ray opaque outer housing and an x-ray transmissive area, attachment means for mounting and aligning said scintillator array assembly adjacent said x-ray transmissive area, means for mounting and aligning said multi-channel photomultiplier tube, and integral alignment means for mounting and aligning said fiber optic taper;

said attachment means comprising an x-positioning screw, a spring-loaded x-return pin, a y-positioning screw, and a spring-loaded y-return pin;

said attachment means further comprising an adjustment plate and a plurality of attachment screws, said scintillator array assembly rigidly attached to said adjustment plate with said attachment screws;

said x-positioning screw biasing said adjustment plate against said spring-loaded x-return pin, said adjustment plate positionally adjusted in the x-direction by rotation of said x-positioning screw; and said y-positioning screw biasing said adjustment plate against said spring-loaded y-return pin, said adjustment plate positionally adjusted in the y-direction by rotation of said y-positioning screw, said y-positioning screw biasing said adjustment plate along a positional direction perpendicular to the positional direction which said x-positioning screw is biasing said adjustment plate.

3. The multi-detector array assembly of claim 2 wherein said attachment means further comprise a rotational-positioning screw, a spring-loaded rotational-return pin, and a rotational bracket;

a tongue of said x-ray opaque outer housing is disposed between said rotational bracket, said rotational-positioning screw biasing said tongue against said rotational-return pin, said x-ray opaque outer housing rotationally adjusted by rotation of said rotational-positioning screw.

4. A multi-detector array assembly comprising a scintillator array assembly, a fiber optic taper, a multi-channel photomultiplier tube, and a multi-detector housing;

said scintillator array assembly comprising a plurality of scintillator elements, each of said scintillator elements comprising a material which proportionally produces light photons when x-ray photons strike each of said scintillator elements;

said multi-channel photomultiplier tube comprising a plurality of photodetector elements, each of said photodetector elements comprising a light detector and a electrical signal generator, said electrical signal generator outputs discrete electrical signals in proportion to level of said light photons detected by said light detector;

said fiber optic taper comprising a plurality of fiber optic cables, each of said fiber optic cables comprising an input face and an output face, said input face substantially adjacent said scintillator elements, said output face substantially adjacent said photodetector elements;

said multi-detector housing comprising an x-ray opaque outer housing and an x-ray transmissive area, attachment means for mounting and aligning said scintillator array assembly adjacent said x-ray transmissive area, integral alignment means for mounting and aligning said fiber optic taper, and means for mounting and aligning said multi-channel photomultiplier tube; and said integral alignment means comprising an adjustment collar and a plurality of adjustment screws, said adjustment collar containing a centrally formed opening, said fiber optic taper disposed in said centrally formed opening, said adjustment screws disposed equidistantly around said adjustment collar, said adjustment collar positionally adjusted by manipulating said adjustment screws, said fiber optic taper aligned by positional adjustment of said adjustment collar.

* * * * *